United States Patent
Farzam et al.

(10) Patent No.: US 11,517,659 B2
(45) Date of Patent: Dec. 6, 2022

(54) METHODS FOR CREATING AND IMPLEMENTING A PERSONALIZED SITE ROTATION PLAN

(71) Applicant: Montmed Inc., Montréal (CA)

(72) Inventors: Amir Farzam, Montréal (CA); Allison Olenginski, Dillon, CO (US)

(73) Assignee: Montmed Inc., Montreal (CA)

( * ) Notice: Subject to any disclaimer, the term of this patent is extended or adjusted under 35 U.S.C. 154(b) by 182 days.

(21) Appl. No.: 16/692,688

(22) Filed: Nov. 22, 2019

(65) Prior Publication Data

US 2020/0155754 A1 May 21, 2020

Related U.S. Application Data

(63) Continuation of application No. 15/193,546, filed on Jun. 27, 2016, now Pat. No. 10,485,919, which is a
(Continued)

(30) Foreign Application Priority Data

Jun. 25, 2015 (CA) .................................. CA 2895103

(51) Int. Cl.
*A61M 5/00* (2006.01)
*A61M 5/42* (2006.01)
*A61M 37/00* (2006.01)

(52) U.S. Cl.
CPC ............ *A61M 5/002* (2013.01); *A61M 5/003* (2013.01); *A61M 5/427* (2013.01);
(Continued)

(58) Field of Classification Search
CPC .. A61M 5/002; A61M 37/0076; A61M 5/003; A61M 5/427; A61M 2205/6063;
(Continued)

(56) References Cited

U.S. PATENT DOCUMENTS

| 4,657,021 A | 4/1987 | Perry et al. |
| 7,645,264 B2 | 1/2010 | Marsh et al. |

(Continued)

FOREIGN PATENT DOCUMENTS

WO 2015085019 A1 6/2015

OTHER PUBLICATIONS

Cramer, J. et al. "A Systematic Review of Adherence with Medication for Diabetes" Diabetes Care, May 2004, pp. 1218-1224, vol. 27, No. 5.
(Continued)

*Primary Examiner* — Lauren P Farrar
*Assistant Examiner* — Hamza A Darb
(74) *Attorney, Agent, or Firm* — Larson & Anderson, LLC

(57) ABSTRACT

A kit to facilitate creation of and compliance with a personalized injection site rotation plan includes a plurality of disposable injection devices adapted for giving an injection of a medication to a patient in need thereof, each disposable injection device having a permanent, distinctive mark that may be the same as or different from the distinctive mark on other disposable injection devices in the kit; and a plurality of user-defined association tools, wherein for each unique distinctive mark on a disposable injection device, at least one user-defined association tool has a distinctive mark that corresponds to the unique distinctive mark.

11 Claims, 8 Drawing Sheets

Related U.S. Application Data continuation-in-part of application No. PCT/CA2015/051047, filed on Oct. 19, 2015.

(52) U.S. Cl.
CPC ..... *A61M 37/0076* (2013.01); *A61M 2205/59* (2013.01); *A61M 2205/6045* (2013.01); *A61M 2205/6063* (2013.01)

(58) Field of Classification Search
CPC ...... A61M 2205/59; A61M 2205/6045; A61M 2205/584; A61M 2205/6009; A61M 2205/6081; A61M 2205/60; A01K 11/00; A01K 11/005; A61B 2090/395
See application file for complete search history.

(56) References Cited

U.S. PATENT DOCUMENTS

| | | | |
|---|---|---|---|
| 7,857,138 B2 | 12/2010 | Temple | |
| 8,574,194 B2 | 11/2013 | Taylor | |
| 8,882,706 B2 | 11/2014 | Cronenberg | |
| 9,311,592 B1 | 4/2016 | Vitello et al. | |
| 2005/0101905 A1 | 5/2005 | Merry | |
| 2005/0177129 A1 | 8/2005 | Pacha et al. | |
| 2010/0203489 A1 | 8/2010 | Koster | |
| 2013/0144256 A1 | 6/2013 | Wessel et al. | |
| 2014/0188074 A1 | 7/2014 | Jacques et al. | |
| 2014/0236019 A1 | 8/2014 | Rahum | |
| 2014/0271897 A1 | 9/2014 | Pathak | |
| 2015/0057637 A1 | 2/2015 | Herr | |
| 2017/0028141 A1* | 2/2017 | Fiedler | A61M 5/427 |
| 2017/0056605 A1* | 3/2017 | Kondo | G16H 20/17 |

OTHER PUBLICATIONS

De Coninck, C. et al. "Results and Analysis of the 2008-2009 Insulin Injection Technique Questionnaire survey" Journal of Diabetes, 2010, pp. 168-179, vol. 2.

McDuffie, R. et al. "Empowerment for Diabetes Management: Integrating True Self-Management into the Medical Treatment and Management of Diabetes Mellitus", Ochsner Clinic and Alton Ochsner Medical Foundation, 2001, pp. 149-157, vol. 3, No. 3.

* cited by examiner

METHODS FOR CREATING AND IMPLEMENTING A PERSONALIZED SITE ROTATION PLAN

CROSS-REFERENCE TO RELATED APPLICATIONS

This application is a continuation of U.S. patent application Ser. No. 15/193,546, filed Jun. 27, 2016, now U.S. Pat. No. 10,485,919B2, Issued on Nov. 26, 2019, which is a continuation-in-part of International Application PCT/CA2015/051047, filed Oct. 19, 2015, which claims the benefit of Canadian Patent Application No. 2,895,103, filed Jun. 25, 2015, all of which are incorporated herein by reference.

FIELD OF THE INVENTION

The present invention relates to medical devices and, more specifically, to kits and methods to encourage self-care by assisting a patient in developing and following an injection site rotation plan.

BACKGROUND

Administration of injections causes trauma to underlying tissues. In many cases, such as when vaccines are administered in a doctor's office or a peripheral venous catheter is placed during a short a hospital stay, the tissue is only exposed to medication for a short period of time and the tissue has an opportunity to heal before it is subjected to more trauma. As a result, few complications occur when injections occur sporadically. However, for those patients that have chronic conditions or diseases, such as diabetes, repeatedly injecting the same area of the body or placing infusion sets or similarly invasive devices in the same area of the body can result in complications that affect a patient's ability manage his or her disease. Rotation of injection/insertion sites is required for effective management of chronic conditions.

In some cases, repeated injections result in the formation of masses of fibrocollagenous scar tissue at the injection site. Localized lipodistrophy, or loss of fat, may also occur as a result of trauma and also as a result of exposure to medications or treatments being administered subcutaneously. The repeated subcutaneous administration of insulin in the same area can also lead to lipohypertrophy, the accumulation of hardened pocket of fat under the skin. Lipohypertrophy occurs at the injection sites of diabetic patients because insulin has a hypertrophic effect on fat cells—it causes fat cells to get larger.

When the underlying tissue around an injection site changes, the body's ability to absorb whatever is being injected into that site also changes. As a result, the efficacy of medications delivered into the subcutaneous tissue changes. In the case of patients having diabetes, changes in absorption can contribute to variable glucose levels (hypoglycemia or hyperglycemia), leakage and therefore loss of the injected insulin dose from under the skin, and reduced or slowed absorption of insulin resulting in gradual increases in insulin dosage (as much as a 20% increase over the course of a year). Changes in underlying tissue can also reduce the availability of healthy injection sites to a patient.

An international survey on insulin injection technique (DeConinck C et al., "*Results and analysis of the 2008-2009 insulin injection technique questionnaire survey*", Journal of Diabetes 2010; 2:168-179) revealed that: 47% of the participants had experienced lipohypertrophy and this was associated with repeated injections into a site smaller than a postage stamp. The survey also revealed that 28% of the participants could not remember ever having their injection sites checked by a health care provider. The survey also indicated that higher A1C levels have been reported with patients injecting into lipohypertrophic sites, indicating that lipohypertrophy contributes to changes in insulin absorption. Clearly there exists a need to rotate injection sites and to monitor injection sites for complications in order to effectively manage chronic conditions, such as diabetes, that require repeated injections.

Another factor that contributes to the high rate of lipohypertrophy or similar tissue damage is the reuse of needles/injection devices that are intended to be sterile, disposable, single use items. A recent study by Berard L. et al., "*Injection technique practices in population of Canadians with Diabetes: Results from a recent patient/diabetes educator survey*", Canadian Journal of Diabetes, (2015), Vol. 39, Issue 2, 146-151, indicated that only 60.7% patients dispose of a needle after use (use the needle only one time. The table below shows the number of times a patient uses a single-use needle versus the percentage of patients. Nearly 40% of the population surveyed re-uses single use, disposable needles, with 30.2% of the population reusing these needles 2 to 5 times.

| | Number of time(s) | | | | | | | | | | |
|---|---|---|---|---|---|---|---|---|---|---|---|
| | 1 | 2 | 3 | 4 | 5 | 6 | 7 | 8 | 9 | 10 | Over 10 |
| % patients | 60.7% | 13.0% | 8.4% | 5.2% | 3.6% | 2.3% | 0.8% | 0.4% | 0.2% | 1.0% | 4.4% |

Reuse of needles or injection devices increases trauma at the injection site because a needle is damaged, bent, and/or dulled each time it penetrates the skin. Thus, while reusing a needle might seem economical and convenient, it results in increased trauma at the injection site and increasingly painful injections. Further, reuse of needles increases the opportunity for infection. Devices intended for self-injection/auto-injection vary from syringes having an integrated needle permanently or semi-permanently incorporated to insulin pens whereby a sterile, disposable pen needle is attached to facilitate drug container access allow fluid egress from the container through the needle into the patient to single use pen-style injectors. However, none of these devices intend for the portion of the device that penetrates a patient's skin to be reused. Exemplary devices used to inject self-administered medication via a combination of a pen injector and a sterile, single use pen needle are disclosed in U.S. Pat. No. 7,645,264 B2 (Marsh) or U.S. Pat. No. 8,882,706 B2 (Cronemberg), and in Canadian Patent Application No. 2 858 665 (Herr). Given the high rate of reuse of needles, there also exists a need to remind or prompt a patient or user to use a new needle for each injection to reduce complications that occur as a result of repeated injections at a limited number of injection sites.

In the survey by Berard L. et al. mentioned above, the vast majority of participants (80.4%) injected medication into the abdomen; 36.6% had no explicit injection routine, and 31.4% injected into the same site at the same time each day. Overall, 24.6% of patients observed lipohypertrophy at injection sites, while only 13.3% of diabetes educators observed the same complication. In order to maximize efficacy of an insulin or other injection regimen and minimize complications resulting from repeated injections at the same site, there exists a need to facilitate creation of and compliance with a personalized injection plan for diabetic patients and others patients that receive frequent subcutaneous injections.

U.S. Pat. No. 7,857,138 B2 (Temple) teaches a system for organizing and storing pre-determined dosages of medication by matching indicia on both the storage apparatus and the apparatus containing the medication. The invention by Temple is particularly directed to a method for administering the good dosage but does not resolve the problem of changing needles and injection sites.

US Patent Application Publication Nos. 2013/0144256 A1 (Wessel et al.) and 2014/0188074 A1 (Jacques R. et al.) teach usage of a medical marking apparatus and tattoo activation device containing a medical ink barrel. This method will increase the complications of injection and administration of medication because it adds extra mechanical parts to the injection device and extra steps to each injection. This method might not be well accepted by the patient, because it creates random ink marks on the skin, which can be unpleasant for the patient. A similar injection site marking method is disclosed in U.S. Pat. No. 8,574,194 B2 (Taylor), but has the same drawbacks mentioned above.

International Patent Application No. PCT/US2014/068469 (Fiedler et al.) discloses providing injection devices having removable markers that are pre-associated with different injection sites to facilitate an injection regiment, with the markers being removed from the injection devices and applied to a physical or electronic chart to track compliance with an injection regimen. The removable markers, however, can easily be lost or damage when carrying injection devices, and carrying a chart and applying a sticker to it each time an injection is administered can be burdensome to a patient/user/caregiver. Further, pre-assignment of injection sites can present problems because it does not account for the needs of users or patients. Not all injection sites are suitable for all users, for example, because of the condition of underlying tissue, accessibility, and/or pain. In one embodiment, Fiedler et al. discloses that injection devices can be provided in a compartmentalized container, where each compartment corresponds to part of an injection scheme. In practice, however, users do not carry large containers of injection devices around on a daily basis. A user carries only those injection devices he or she will need for the day (or trip), along with emergency supplies in case of delay. Thus, any association based on compartmentalization will be lost in daily use.

Thus, there exists a need for new tools and methods that can be personalized to the needs of an individual, yet are easy to understand and implement, in order to help patients to integrate regular change of the needle and rotation of injection site to their daily disease management routine.

SUMMARY OF THE INVENTION

The present invention relates to a kit to facilitate creation of and compliance with a personalized injection site rotation plan. The kit includes a plurality of disposable injection devices adapted for giving an injection of a medication to a patient in need thereof, each disposable injection device having a permanent, distinctive mark that may be the same as or different from the distinctive mark on other disposable injection devices in the kit; and a plurality of user-defined association tools, wherein for each unique distinctive mark on a disposable injection device, at least one user-defined association tool has a distinctive mark that corresponds to the unique distinctive mark. The distinctive mark may be a colour, symbol, pattern, letter, number, or any combination thereof. In some embodiments, the plurality of disposable injection devices are disposable pen needles. The user-defined association tools include temporary tattoos, stickers and marking devices; and multiple types of user-defined association tools may be used together.

In some embodiments, the kit includes a disposable injection device dispenser configured to dispense disposable injection devices in a specific sequence. The specific sequence may include providing access to a number of disposable injection devices having a first distinctive mark, next providing access to a number of disposable injection devices having a second distinctive mark, next providing access to a number of disposable injection devices having a third distinctive mark; and next providing access to a number of disposable injection devices having a fourth distinctive mark.

In some embodiments, the kit includes a disposable injection device dispenser configured to dispense disposable injection devices, one at a time, in a randomized order. In other embodiments, the kit includes a disposable injection device dispenser configured to dispense a randomized selection of disposable injection devices to a user simultaneously. The kit may also include a user-operable chance selection device for selection of a specific disposable injection device from the plurality of disposable injection devices dispensed. In some embodiments, the injection device is a pen needle having an outer needle cap, an inner needle cap, and a needle and hub, and the same distinctive mark is present on all three components of the pen needle. In some embodiments, the kit includes a friction reduction tool for evaluating an injection site. The friction reduction tool may include a lubricant.

In some embodiments, the kit includes a body chart, wherein the user-defined association tools include a plurality of markers configured to be applied to the body chart. The body chart may be a digital body chart configured to be displayed on a computing device, and the user-defined association tools are electronic markers configured to be applied to the digital body chart.

The present invention also provides a method for assisting a patient in developing and adhering to an injection routine. The method comprises providing a plurality of disposable injection devices adapted for giving an injection of a medication to a patient in need thereof, each disposable injection device having a distinctive mark that may be the same as or different from the distinctive mark on other disposable injection devices provided; and creating a user-defined association between the plurality of user-defined association tools and injection sites, wherein for each unique distinctive mark on a disposable injection device, at least one user-defined association tool has a distinctive mark that corresponds to the unique distinctive mark.

In other implementations, the user-defined association may be created between the association tool and other parameters of a personalized injection plan including injection time of day, and injection site.

A method for assisting a patient in developing and adhering to a personalized injection site rotation plan, in accordance with the present invention, includes providing a plurality of disposable injection devices adapted for giving an injection of a medication to a patient in need thereof, each disposable injection device having a distinctive mark that may be the same as or different from the distinctive mark on other disposable injection devices provided; providing a plurality of user-defined association tools, wherein for each unique distinctive mark on a disposable injection device, at least one user-defined association tool has a distinctive mark that corresponds to the unique distinctive mark; and creating a user-defined association between each unique distinctive mark and an injection site. In some embodiments, the plurality of user-defined association tools are temporary tattoos or stickers for affixing to human skin, and the method further includes applying at least one tattoo or sticker to its associated injection area on the body. In some embodiments, the method includes dispensing the plurality of disposable injection devices in a specific sequence indicative of an injection site rotation scheme. In other embodiments, the method includes dispensing several of the plurality of disposable injection devices simultaneously in a random fashion, and allowing a user to select from the dispensed disposable injection devices to create an injection site rotation scheme.

BRIEF DESCRIPTION OF THE DRAWINGS

The above and other aspects, features, and advantages of the invention will become more readily apparent from the following description, reference being made to the accompanying drawings in which.

DETAILED DESCRIPTION

Figure 1:
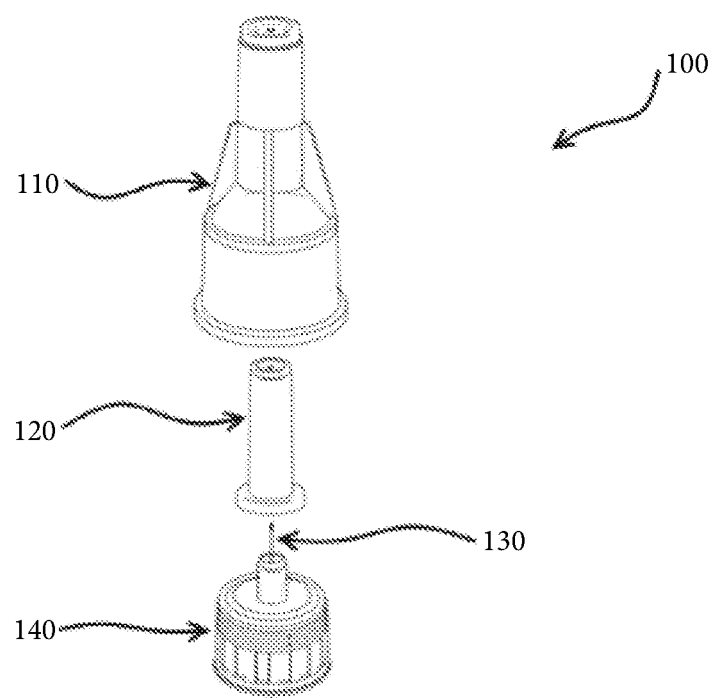
FIG. 1 illustrates an exemplary disposable injection device in accordance with the present invention.

Reference throughout the specification to "one embodiment," "another embodiment," "an embodiment," "some embodiments," and so forth, means that a particular element (e.g., feature, structure, property, and/or characteristic) described in connection with the embodiment is included in at least one embodiment described herein, and may or may not be present in other embodiments. In addition, it is to be understood that the described element(s) may be combined in any suitable manner in the various embodiments. Further, for the purposes of this application, it should be appreciated that a disposable injection device may be any injection device, infusion device, or the like in which the portion of the injection device, infusion set, or the like that punctures the skin is disposable and intended for single use. Such devices include, but are not limited to, single use, disposable pen-style injectors; reusable pen-style injectors configured for use with a single use, disposable pen needle; syringes having an integrated needle permanently or semi-permanently incorporated therein; infusion sets configured for use with insulin pumps or other subcutaneous drug delivery systems; safety pen needles, and the like. Additionally, while the examples presented herein relate to diabetes, it should be appreciated that the kits and methods described herein can be applied to any situation where injections are frequently required, without departing from the scope of the invention.

The term "user," as used herein, refers to anyone that might administer an injection. Users include patients themselves; caregivers such as parents, guardians, home health aides, and the like; health care providers such as physicians, physician assistants, nurses, nurses aides, and the like; and any other individual that might assist in administering an injection. In the context of "user-defined" elements of the invention, it should be appreciated that user definitions are based on the specific needs of the patient and his or her circumstances, and therefore are personalized. Preferably, the patient creates these associations. However, in circumstances where the patient is unwilling or unable to create the associations, or requires assistance in administration of injections, other users, such as caregivers and health care providers, may assist in creation of the associations without departing from the scope of the invention. Additionally, the term "injection site," as used herein, refers to an area where an injection can or will be administered. As used herein, this may include a specific injection location, a larger injection zone, or a body area where an injection can/will be administered, without departing from the scope of the invention.

Adherence to prescribed medication regimes and self-care protocols is essential to the management of chronic diseases such as diabetes, but can be difficult for patients. Cramer J A. (2004). A systematic review of adherence with medications for diabetes. *Diabetes Care,* 27(5), 1218-1224. It has been suggested that diabetes management can be improved by supporting patients while also allowing patients to take control of their own healthcare decisions. McDuffie, R. H., Struck, L., & Burshell, A. (2001). Empowerment for Diabetes Management: Integrating True Self-Management into the Medical Treatment and Management of Diabetes Mellitus. *The Ochsner Journal,* 3(3), 149-157. As discussed above, patients and caregivers often have difficulty adhering to an injection site rotation protocol, and many patients and caregivers fail to use a new, sharp, sterilized needle for each injection. Individually or in combination, disregard for these well-accepted protocols can result in complications that slow the body's ability to absorb insulin, making the same amount of insulin less effective for a patient over time. It is not surprising that patients and/or caregivers find some prescribed protocols difficult to adhere to based on individual circumstances or situations and, in some cases, lack of knowledge negatively impacts compliance despite the best of intentions.

The present invention seeks to improve compliance with self-care protocols and optimize the effects of prescribed medication regimes by empowering a patient to develop and personalize an injection site rotation protocol that works for that individual and his or her circumstances, and providing a kit with relevant tools to successfully develop and implement a patient or caregiver defined protocol. This allows a patient and/or his or her caregiver(s) to take ownership of a protocol and to take advantage of the associations that make the most sense in their daily lives in order to improve compliance and, ultimately, disease management.

FIG. 1 illustrates an exemplary disposable injection device 100 in accordance with the present invention. Disposable injection device 100 includes an outer needle cap 110, an inner needle cap 120, and a needle cannula 130 attached to a hub 140.

FIGS. 2-5 illustrate exemplary kits in accordance with the present invention. Each kit includes a plurality of disposable injection devices, each disposable injection device having a permanent or integral distinctive mark. It should be appreciated that the number of injection devices can be varied in each kit. Further, while 4 unique distinctive marks are illustrated for exemplary purposes, it should be appreciated that the number of unique distinctive marks can be varied in each, as can the number of disposable injection devices displaying each unique mark. Each kit also includes a plurality of user-defined association tools that correspond to the unique distinctive marks present in each kit. Distinctive marks include colours, patterning, letters, numbers, symbols, and the like. It should be appreciated that the number and type of user-defined association tools may be varied without departing from the scope of the invention. Preferably, each kit includes at least one user-defines association tool for each unique distinctive mark that appears on the disposable injection devices. However, in some embodiments, one or more of the unique distinctive marks in the kit may not have a corresponding user-defined association tool. Further, in some embodiments, multiple user-defined association tools correspond to each unique distinctive mark in order to provide flexibility for a user.

Figure 2:
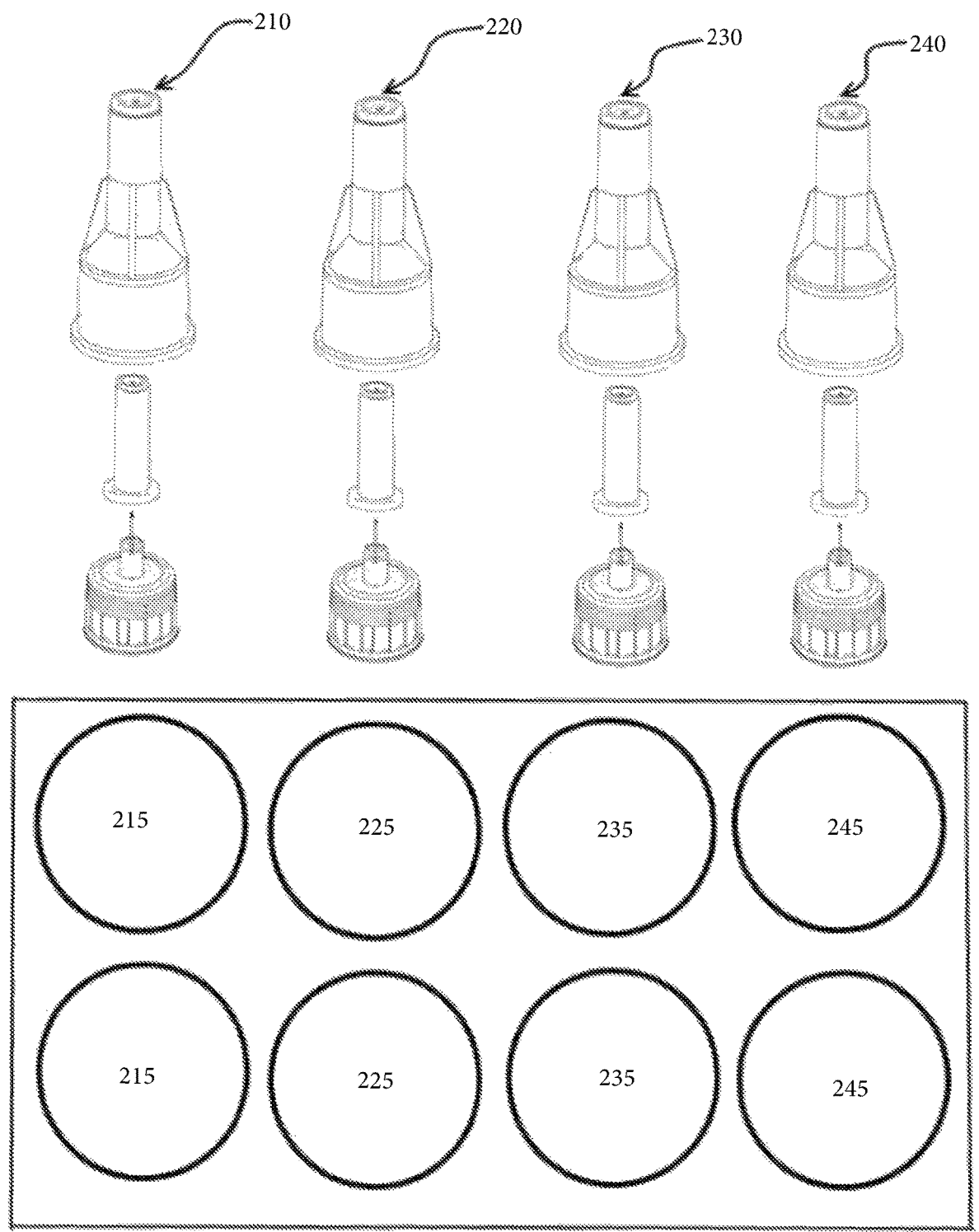
FIGS. 2-5 illustrate exemplary kits in accordance with the present invention.

FIG. 2 illustrates a portion of an exemplary kit that includes disposable injection devices 200 having 4 different colours as distinctive marks, and user-defined association tools 250 that correspond to those distinctive marks. Specifically, disposable injection device 210 is a first colour, disposable injection device 220 is a second colour, disposable injection device 230 is a third colour, and disposable injection device 240 is a fourth colour. It should be appreciated that the inclusion of four disposable injection devices in this kit is for illustration purposes only, and the number of disposable injection devices associated with each distinctive mark may be varied without departing from the scope of the invention. In some embodiments, it is preferable to have equal numbers of disposable injection devices associated with each unique identifier so that an even rotation cycle can be achieved. As noted above, the disposable injection devices may be pen needles, syringes, infusion sets, etc. Where the disposable injection devices have multiple parts, such as in the case of pen needles that have an outer needle cap, an inner needle cap, and a needle cannula attached to a hub, it is preferable that the distinctive mark be permanent and present on at least each separable part of the pen needle. In some embodiments, it is preferable that the distinctive mark that are visible when the parts the disposable injection device are assembled. In some embodiments, one or two parts of the pen needle may be transparent so that the distinctive identifier remains visible at all times. In other embodiments, the distinctive mark may appear on all parts of the pen needle assembly. Thus, the distinctive mark persists on the disposable injection device at all times and through all circumstances, including when parts of the disposable injection device are separated.

A plurality of user-defined association tools 250 are included in the kit. These user-defined association tools display the same distinctive marks present on the disposable injection devices, though the exact number of user-defined association tools can be varied without departing from the scope of the invention. Preferably, at least one user-defined association tool displays each unique distinctive mark. In the kit shown, user-defined association tools 215 display the colour associated with disposable injection device 215, user-defined association tools 225 display the mark associated with disposable injection device 220, user-defined association tools 235 display the mark associated with disposable injection device 230, and user-defined association tools 245 display the mark associated with disposable injection device 240.

Figure 3:
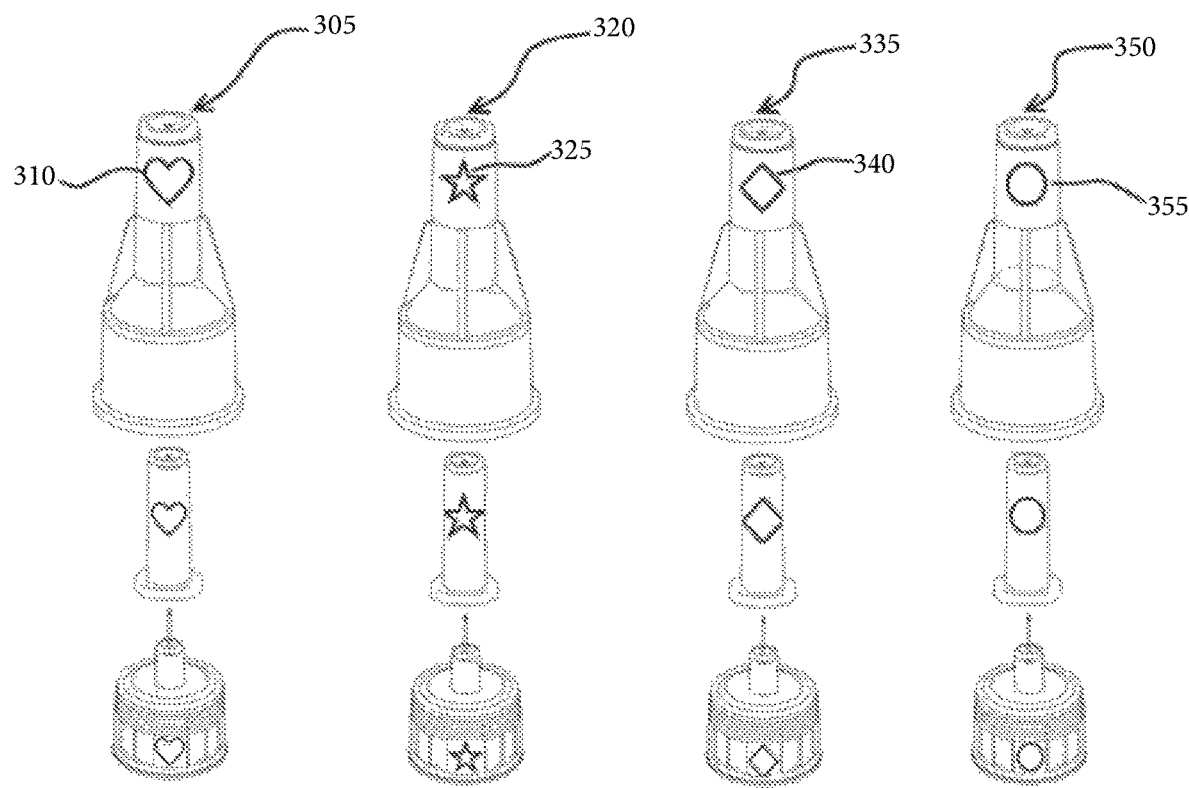
Figure 3:
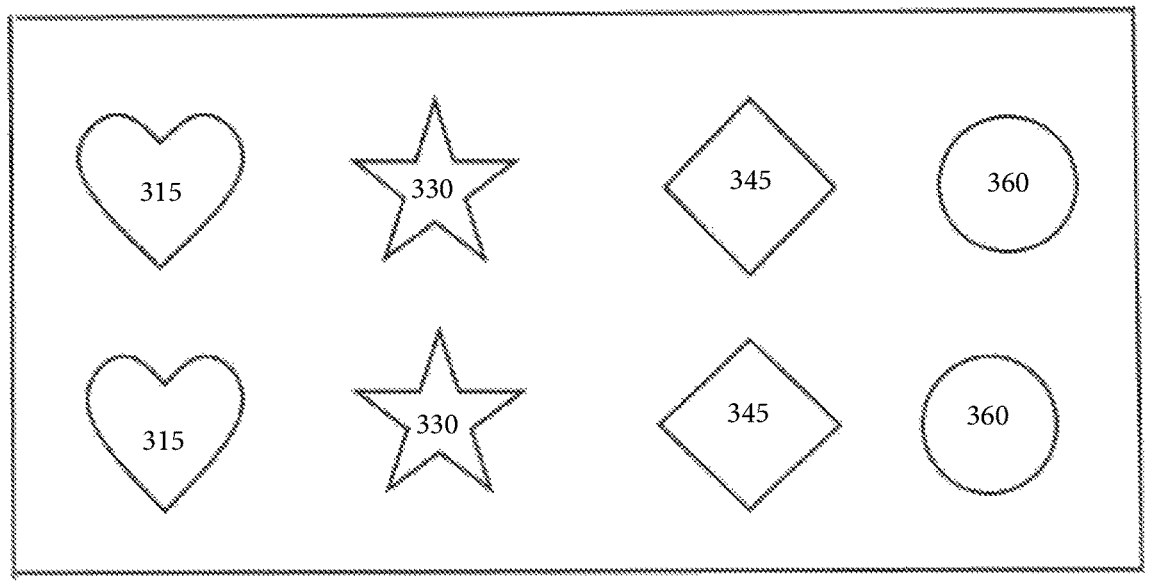
Figure 4:
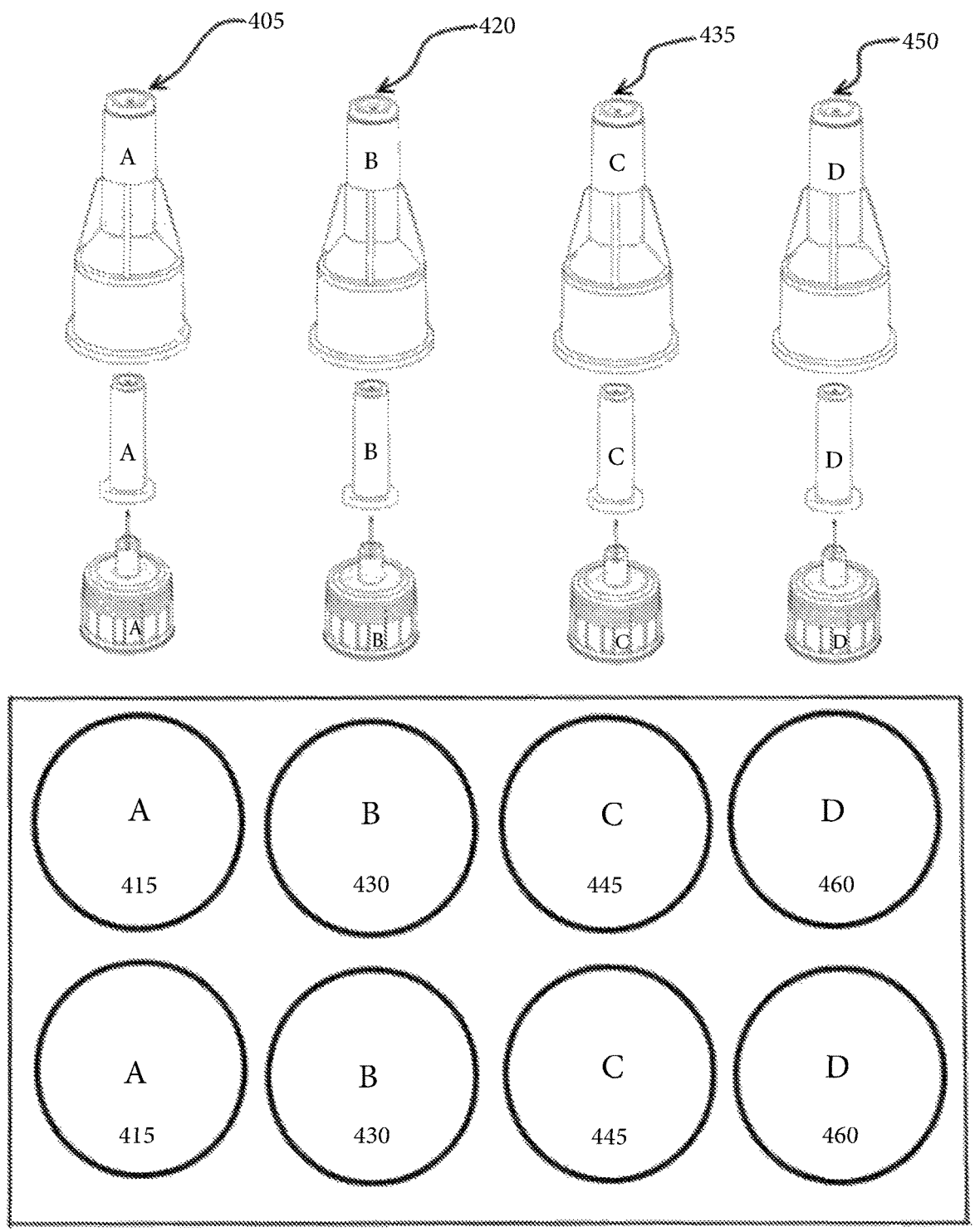
Figure 5:
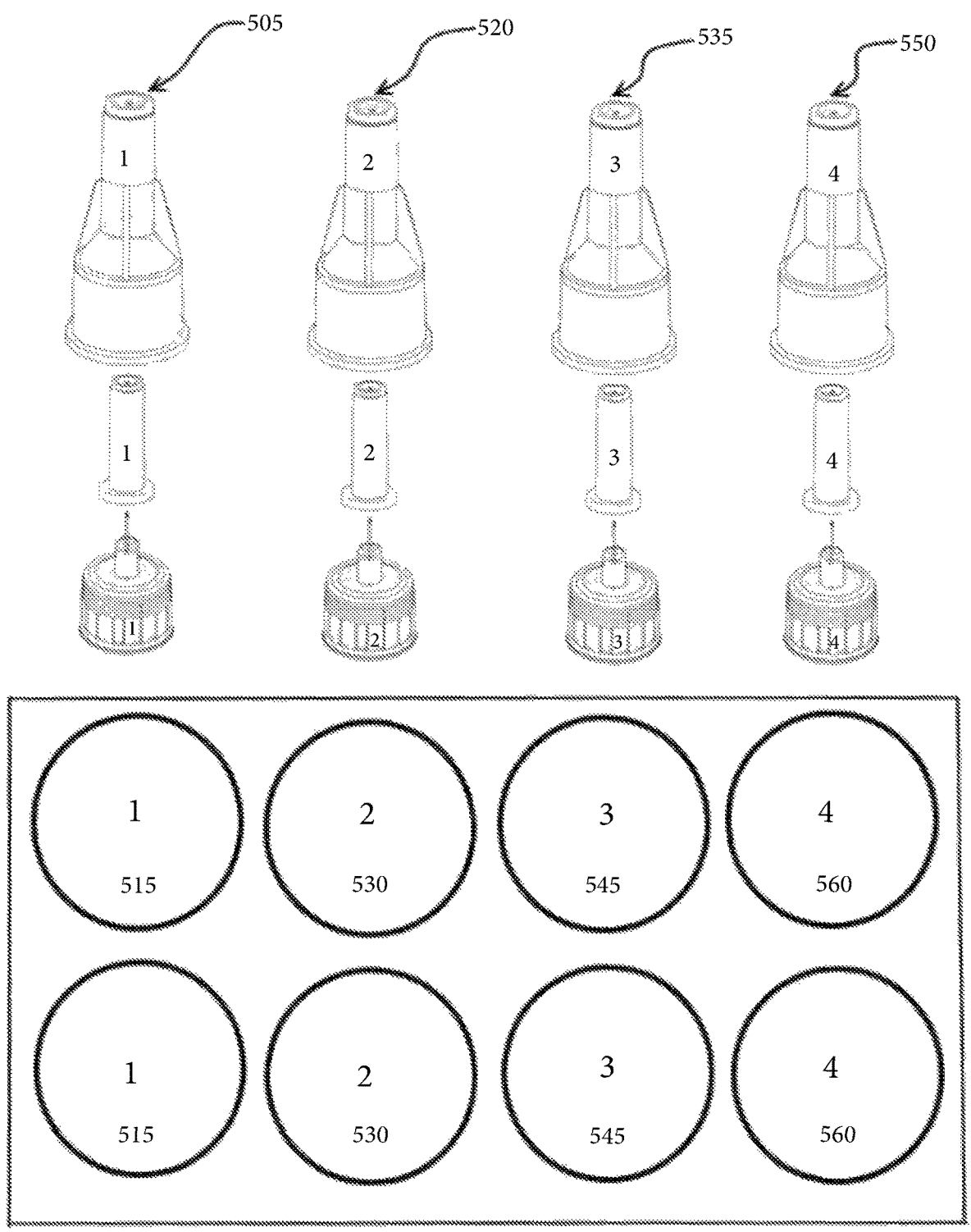

FIGS. 3-5 illustrate portions of kits in which the distinctive mark has been varied. For example, in FIG. 3, the distinctive marks are shapes, and the user-defined association tools mimic the shape of the respective unique distinctive marks. As shown in FIG. 3, disposable injection device 305 is distinctively marked by a heart 310, and has corresponding user-defined association tools 315; disposable injection device 320 is distinctively marked by a star 325, and has corresponding user-defined association tools 330; disposable injection device 335 is distinctively marked by a diamond 340, and has corresponding user-defined association tools 345; and disposable injection device 350 is distinctively marked by a circle 355, and has corresponding user-defined association tools 360. FIG. 4 illustrates a portion of a kit where letters are used as distinctive marks. In FIG. 4, disposable injection device 405 is distinctively marked by the letter "A", and has corresponding user-defined association tools 415; disposable injection device 420 is distinctively marked by the letter "B", and has corresponding user-defined association tools 430; disposable injection device 435 is distinctively marked by the letter "C", and has corresponding user-defined association tools 445; and disposable injection device 450 is distinctively marked by the letter "D", and has corresponding user-defined association tools 460. FIG. 5 illustrates a kit where numbers are used as distinctive marks. In FIG. 5, disposable injection device 505 is distinctively marked by the number "1", and has corresponding user-defined association tools 515; disposable injection device 520 is distinctively marked by the number "2", and has corresponding user-defined association tools 530; disposable injection device 535 is distinctively marked by the number "3", and has corresponding user-defined association tools 545; and disposable injection device 550 is distinctively marked by the number "4", and has corresponding user-defined association tools 560. It should be appreciated that the type and number of distinctive marks may be varied without departing from the scope of the invention.

If, for example, a kit contains 35 disposable injection devices, each disposable injection device has a distinctive mark that may be the same as or different from the distinctive mark on other disposable injection devices in the kit. Some of the disposable injection devices will share the same mark. However, there may be a limited number of unique marks. For example, if there are 7 unique marks, 5 disposable injection devices would display the first mark, 5 disposable injection devices would display the second mark, 5 disposable injection devices would display the third mark, 5 disposable injection devices would display the fourth mark, 5 disposable injection devices would display the fifth mark, 5 disposable injection devices would display the sixth mark, and 5 disposable injection devices would display the seventh mark. The kit would contain at least 7 user-defined association tools, and each user-defined association tool would display a unique mark. Duplicate user-defined association tools may be present without departing from the scope of the invention. In practice, a user creates an association between each unique distinctive mark present in the kit and an injection site. Preferably, the user memorializes the association using a user-defined association tool.

User-defined association tools allow the user to create and memorialize unique, personal associations for an injection site rotation scheme, rather than using pre-defined relationships that may not be consistent with the patient's preferred injection sites. In some implementations, the user-defined association tools may be stickers, temporary or non-permanent tattoos configured to be applied to the skin by a user, markers or stamps using a skin-safe temporary ink, or the like. In this implementation, the user creates an association between a distinctive mark and an injection site by applying different or unique user-defined association tools to different injection sites on the body. In some embodiments, one or more user-defined association tool may be repeated while the others applied are unique. For example, a user may apply a temporary tattoo having the same distinctive mark to a body part that is repeated, because the user associates that mark generally with the arms as an injection site, and the user has two arms. Further, in some embodiments, such as those intended for children, the user-defined association tools may be embellished with characters such as superheroes in order to increase the patient's interest in the association tool and associated injection site. In still other embodiments, the user-defined association tools may be shaped to define multiple specific injection sites in an injection area to further encourage injection site rotation.

Figure 6A:
FIGS. 6A, 6B, 6C, and 6D illustrate user-defined association tools in accordance with the present invention.

FIG. 6A illustrates another user-defined association tool in accordance with the present invention. In FIG. 6A, the user-defined association tool 600 is a tattoo, sticker, or other marker configured to be applied to the body in a non-permanent (temporary) fashion such as via adhesive, transfer of pigment, or the like. User-defined association tools of multiple colors and/or style images may be presented without departing from the scope of the present invention. The user-defined association tool illustrated in FIG. 6A can serve multiple functions. First, the design and/or colour of the user-defined association device serves as a decorative visual reminder of the injection site, and the disposable injection device to be used with that particular injection site, as discussed above. Second, the appearance of the user-defined association tool serves as a reminder for a user to rotate from injection site to injection site in a specific area on the body. The stylized sun 600 illustrated in FIG. 6A, for example, includes 7 rays or points around its perimeter that act as direction guides for injection site rotation. This provides guidance to a user without providing an explicit template, providing increased flexibility for a user to customize his or her injection site rotation plan. It should be appreciated that the design and number of direction guides present on a user-defined association tool may be varied without departing from the scope of the invention.

In one exemplary embodiment, a kit includes a plurality of user-defined association tools having the same stylized design, including features that direct injection site rotation, but each user-defined association tool is a different colour. A plurality of disposable injection devices are included in the kit, and the colours (or other distinctive marks) of the disposable injection devices correspond to the colours (or other distinctive marks) of the user-defined association devices. Preferably, the colours/distinctive marks of the disposable injection devices in the kit are evenly distributed (i.e., 10 disposable injection devices of each colour/distinctive mark). Such a kit can be used in different ways. First, a user could apply a single user-defined association tool to his or her body; and then sequence through all injection sites indicated by that user-defined association device using the correspondingly marked disposable injection devices; apply a second user-defined association device to his or her body; and repeat the process. Alternatively, a user could apply multiple user-defined association devices to different body parts, and then create a different plan for rotation. For example, the plan may involve using one injection site associated with each user-defined association tool before using a second injection site at each user-defined association tool. This plan would allow for greater dispersion of injection sites. In still other implementations, the user-defined association tool may include multiple distinctive marks. For example, with respect to the design illustrated in FIG. 6A, each ray in the design may be of a unique colour or distinctive mark that corresponds to the colour/mark on a disposable injection device, and the colour/mark association can be used to rotate through different injection sites in the same general area of the body.

Figure 6B:
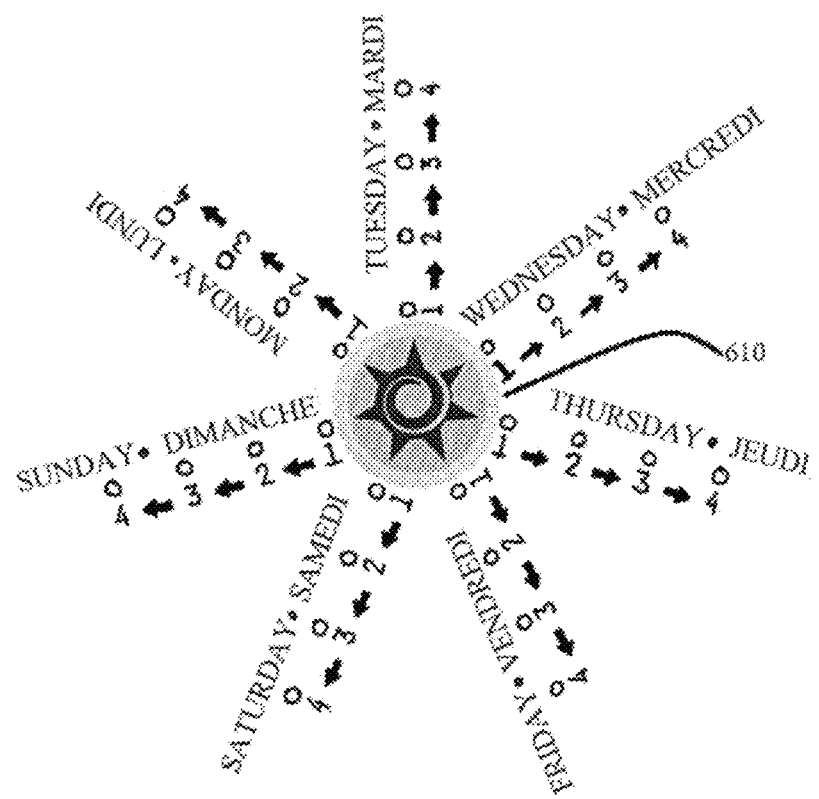

FIG. 6B illustrates an injection site guide that may be included in a kit in accordance with the present invention. At the center of the guide 610 is a reproduction of the design of the user-defined association tool illustrated in FIG. 6A. The guide is intended to be carried with the user, for example, in place of a body chart or similar device, and may be printed on paper or cardstock or the like, or be implemented digitally, for example, as part of an application that is stored on a computer-readable storage medium, executed by a processor, and displayed on a smartphone, tablet, or computer. Each directional indicator or ray of the user-defined association device is provided with an injection scheme. While the guide of FIG. 6B illustrates each ray of the sun being associated with a day of the week, it should be appreciated that the user may create his or her own associations without departing from the scope of the invention. The guide provides a pattern for rotation that a user can apply to his or her own injection sites, either one site at a time, as noted above, or rotating through the same pattern while alternating between different injection sites/user-defined association tools on the body. Further, the rays or directional guides may be coded with distinctive colours or marks, and/or corresponding disposable injection devices may be dispensed in a specific or random sequence to further encourage positive, healthy injection site rotation. The guide may include additional suggestions for healthy injection site rotation, such as instruction on spacing the injection sites.

In still other embodiments, the user-defined association tools may be markers, stamps, or other writing implements that are capable of marking skin. Preferably, the colours/designs/distinctive marks of these user-defined association tools correspond to the colours/designs/distinctive marks of the disposable injection devices, as described above. A user can then make marks of his or her own design at injection sites, providing further options for customization.

Figure 6C:
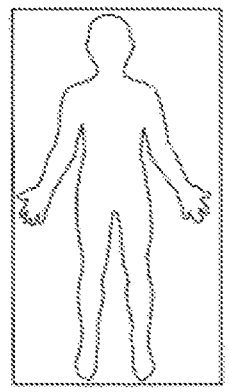
Figure 6D:
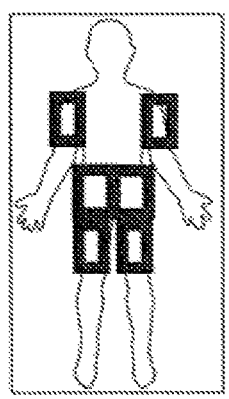

However, not all patients are willing or able to apply stickers or tattoos to his or her skin or to make marks on his or her skin. Accordingly, in some embodiments, the user-defined association tools may be stickers or markers that can be used to memorialize an association between a distinctive mark and a specific injection site. For example, a user-defined association tool may have a blank space where the patient can record the injection site that he or she has assigned to that particular mark. In still other embodiments, the user-defined association tool may be a chart or a body chart such as that illustrated in FIGS. 6C and 6D. The body chart illustrated in FIG. 6C allows a user to define his or her own injection site by applying a sticker or marker to each preferred injection site. The body chart illustrated in FIG. 6D, in contrast, illustrates common injection areas to simplify options for a user that might not have sufficient education to determine his or her own injection sites without some guidance. It should be appreciated that additional user-defined association tools may also be used in conjunction with a body chart to memorialize the association created by the user. It should be appreciated that the charts illustrated in FIGS. 6C and 6D may be implemented in conventional paper formats, or may be implemented digitally via an application that runs on a computing device such as a smartphone, tablet, computer, smartboard, or the like. Such an application is be stored via a non-transitory computer-readable storage medium in said computing device, and executed by the processor in order to display the body chart. In some implementations, the application is configured to receive and store input from a user to memorialize associations made by a user between one or more distinctive marks and associated injection sites.

Some users may wish to create their own sequences for rotating through the injection sites. For example, where the distinctive marks are numbers 1-4, and 4 injections are administered each day, the user may choose to label preferred injection sites in the order of use, based on the patient's lifestyle. For example, a teenager that runs cross-country for his or her high school might choose to associate the number 1 with the left thigh for a morning injection, the number 2 with the lower right quadrant of the abdomen for a noon injection, the number 3 with the upper left quadrant of the abdomen for an afternoon injection, and the number 4 with the right thigh for a night injection. By avoiding the legs/thighs before running in gym and after school cross-country practice, the patient will minimize the impact of running on the action of insulin, and hopefully minimize hypoglycemic episodes during athletic events. Further, the student has adjusted injection sites so that they are all accessible without assistance from a caregiver during the school day.

Figure 7:
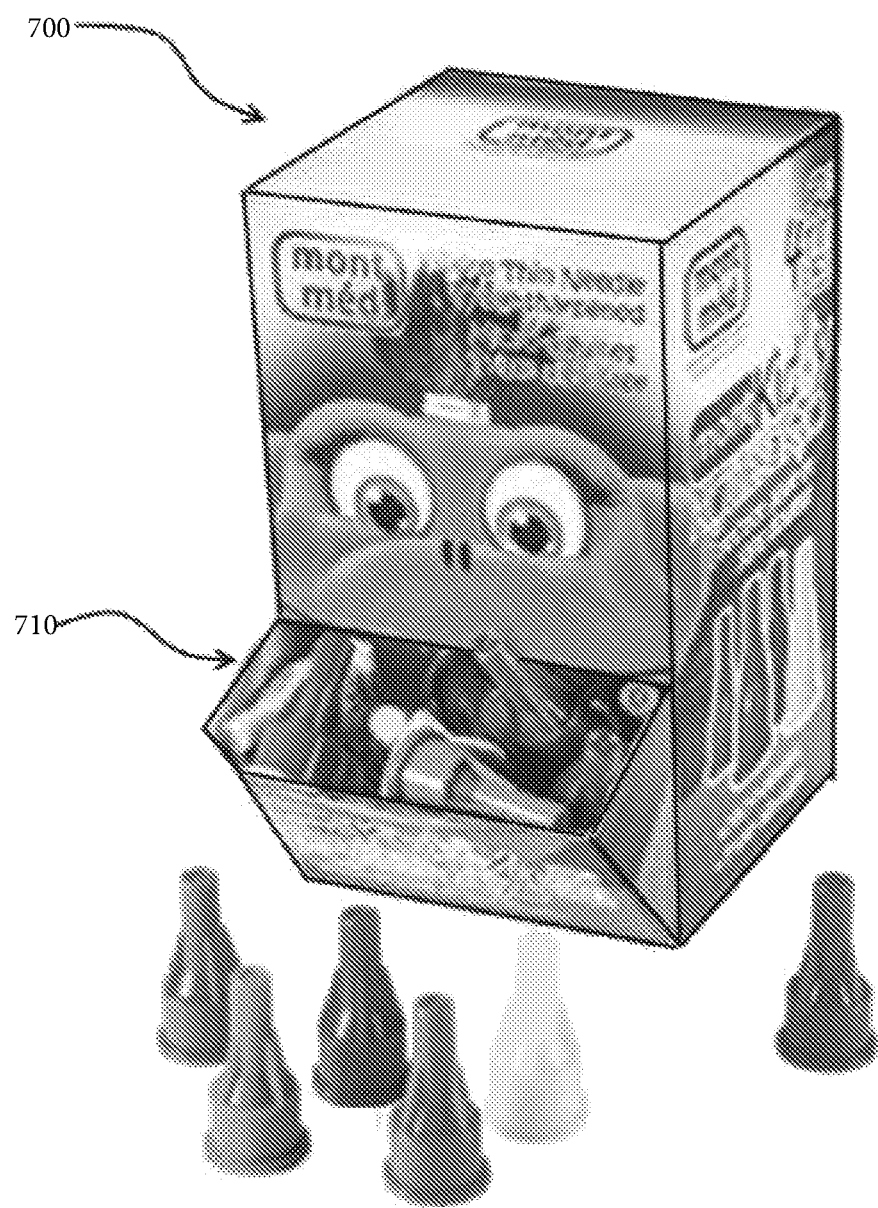
FIG. 7 illustrates a dispenser configured to simultaneously dispense a plurality of disposable injection devices in a randomized fashion, in accordance with the present invention.

Some users will prefer to rely on sequencing or randomization for rotating through injection sites, rather than referring to a chart or generating a sequence of his or her own. Thus, in some embodiments, the kit also includes a disposable injection device dispenser. In some embodiments, the dispenser is configured to dispense the disposable injection device in a specific sequence. For example, in an embodiment where 4 unique marks are present on the disposable injection devices, the dispenser is configured to dispense one disposable injection device displaying each mark before repeating the sequence. In some implementations, specific sequences of marks may be created. In other implementations, disposable injection devices having all of one unique mark are dispensed, then all disposable injection devices having the second mark are dispensed, then all disposable injection devices having the third mark are dispensed, and then all disposable injection devices of the fourth mark are dispensed. In still another embodiment, a dispenser may dispense disposable injection devices in an at least somewhat randomized fashion, such as that illustrated in FIG. 7. In FIG. 7, dispenser 700 includes a large, gravity-fed opening 710 capable of dispensing multiple disposable injection devices simultaneously.

In some embodiments, the user may use the user-defined association tools to create multiple associations, for example, between time of day and injection site. In still other embodiments, multiple types of user-defined association tools may be included in the kit and used in combination to create a system that is sustainable for the user. For example, a sticker may be applied to the injection site on the body to provide a visual reminder for the patient; a marker may be applied to a body chart to memorialize the plan for a health care provider; and a color-coded reminder, matching a unique identifier, may be added to the patient's electronic calendar, such as Google Calendar. Similarly, in some implementations, a tracking chart and/or body chart may be implemented via a computer program stored on a computer-readable storage medium and configured to be executed by the processor of a laptop computer, desktop computer, tablet computing device, smartphone, smartboard, via an application accessible via a web browser, or another computing device. In yet another embodiment, a random number generator can be used to generate an administration sequence at random. In still another embodiment, an app having a pre-programmed sequence or a user-programmable sequence can be included with or used with the kit to provide sequencing information to the patient.

In embodiments where sequencing is provided by an external source such as an app, calendar, chart, or the like, the kit may include multiple containers or dispensers, where the disposable injection devices are grouped according to common distinctive marks. In still other embodiments, the kit may include disposable injection devices that are grouped into packages or dispensers based on the number of injections to be administered during a day or other specified time, so that the patient does not need to carry an excessive number of disposable injection devices.

In some embodiments, such as those targeted at juvenile patients, additional features may be added to the kit to make the injection site rotation protocol more interesting or appealing. For example, when the kit includes a randomized dispenser that dispenses multiple disposable injection devices simultaneously such as that illustrated in FIG. 7, a spinner displaying distinctive marks, dice having sides marked with distinctive marks, or another chance or randomized selection device can be employed by the user to select which disposable injection device to use next. In still further embodiments, the kit may include a tracking device to encourage compliance by providing feedback on progress. In some implementations, the tracking device might be an app that has game-like qualities, such as animation and sound, that provide and indicator of progress through a successful injection site rotation scheme and/or positive feedback for the user, and reinforce positive associations with compliance. In other embodiments, the tracking device might be a coloring page and accompanying marking devices such as crayons, and a patient can color with an appropriately colored marking device to memorialize successful administration of an injection.

Administering daily medication to children can be challenging. The use of the present invention facilitates starting the conversation about diabetes in a neutral way without putting guilt or pressure on the patient. The dialogue can be started by asking which color needle was used for the previous injection or asking which color they prefer to use for the current injection. The use of the present invention also allows empowering children by involving the in decision-making about their diabetes management.

Additionally, in some embodiments, a kit according to the present invention may further include a friction reduction tool to facilitate evaluation of a potential injection site for irregularities such as scar tissue and lipohypertrophy that may affect absorption of whatever medication is administered via subcutaneous injection. The friction reduction tool may be a lubricant, such as a gel or liquid lubricant safe for application to human skin, or a friction reduction pad. A friction reduction pad, such as that described in U.S. Pat. No. 4,657,021, typically includes two layers of a smooth, pliable material separated by and enclosing a lubricant. The lubricant is preferably a liquid lubricant, such as a silicone lubricant. When the friction reduction tool is placed against a potential injection site, a user can palpate the potential injection site through the tool. The lubricant reduces the friction between the user's fingers and the skin, and serves to amplify or enhance the user's sense of touch and facilitate better discernment of irregularities in tissue density and distribution that may not be detected visually. Thus, a friction reduction tool facilitates the selection of healthy injection sited by a user.

Whether the patient is a child or an adult, by allowing the patient to make his or her own associations, it is possible to encourage positive self-care behavior without posing any risk or negative impacts to diabetes management.

While illustrative and presently preferred embodiments of the invention have been described in detail hereinabove, it is to be understood that the inventive concepts described herein may be varied without departing from the scope of the invention.

What is claimed is:

1. A method for creating and facilitating compliance with a personalized injection site rotation plan for a user, comprising:
   identifying a plurality of injection sites suitable for the user;
   identifying a plurality of unique distinctive marks;
   for each of the plurality of injection sites, creating a user-defined association between one of the plurality of unique distinctive marks and one of the plurality of identified injection sites, such that each of the plurality of identified injections sites is associated with a different unique distinctive mark;
   memorializing each user-defined association via a user-defined association tool, wherein said user-defined association tool includes a distinctive mark that corresponds to the unique distinctive mark associated with the user-defined association; and
   creating the personalized injection site rotation plan for the user by defining a sequence of unique distinctive marks for the user to follow, wherein each unique distinctive mark identifies an associated injection site.

2. A method according to claim 1, the method further comprising:
   administering an injection in accordance with the defined sequence.

3. A method according to claim 2, wherein the sequence is cued by display of one of the unique distinctive marks.

4. A method according to claim 1, wherein the unique distinctive marks are colors.

5. A method according to claim 1, wherein the unique distinctive marks are shapes.

6. A method according to claim 1, wherein the unique distinctive marks are symbols.

7. A method according to claim 1, wherein memorializing the association via a user-defined association tool comprises marking the injection site with a unique distinctive mark on a body chart.

8. A method according to claim 1, wherein the sequence of unique distinctive marks is generated using a pseudo-random generator.

9. A method according to claim 1, wherein the sequence of unique distinctive marks is created by the user.

10. A method for creating and facilitating compliance with a personalized injection site rotation plan for a user, comprising:
    identifying a plurality of injection sites suitable for the user;
    identifying a plurality of unique distinctive marks;
    for each of the plurality of injection sites, creating a user-defined association between one of the plurality of unique distinctive marks and one of the plurality of identified injection sites, such that each of the plurality of identified injections sites is associated with a different unique distinctive mark;
    memorializing each user-defined association via a user-defined association tool, wherein said user-defined association tool includes a distinctive mark that corresponds to the unique distinctive mark associated with the user-defined association; and
    presenting one of the plurality of unique distinctive marks to the user prior to injection to indicate an associated injection site and wherein each of the plurality of unique distinctive marks is presented in a user-defined sequence.

11. The method according to claim 10, wherein the sequence in which each of the plurality of unique distinctive marks is presented is determined by a pseudo-random generator.

* * * * *